United States Patent [19]

Gyure

[11] Patent Number: 5,704,920
[45] Date of Patent: Jan. 6, 1998

[54] MANUALLY DRIVEN NEEDLE SHIELD ASSEMBLY

[75] Inventor: Sandor Gyure, West Orange, N.J.

[73] Assignee: Becton, Dickinson and Company, Franklin Lakes, N.J.

[21] Appl. No.: 649,376

[22] Filed: May 17, 1996

[51] Int. Cl.$^6$ .................................... A61M 5/00
[52] U.S. Cl. .................. 604/192; 604/263; 128/919
[58] Field of Search ........................... 604/110, 192, 604/187, 263; 128/919

[56] References Cited

U.S. PATENT DOCUMENTS

| | | | |
|---|---|---|---|
| 2,559,474 | 7/1951 | Son | 128/215 |
| 2,739,591 | 3/1956 | Yochem | 128/218 |
| 4,573,976 | 3/1986 | Sampson et al. | 604/198 |
| 4,738,663 | 4/1988 | Bogan | 604/198 |
| 4,790,828 | 12/1988 | Dombrowski et al. | 604/198 |
| 4,886,503 | 12/1989 | Miller | 604/192 |
| 4,892,521 | 1/1990 | Laico et al. | 604/192 |
| 4,915,696 | 4/1990 | Feimer | 604/192 |
| 4,994,046 | 2/1991 | Wesson et al. | 604/198 |
| 5,026,356 | 6/1991 | Smith | 604/192 |
| 5,215,534 | 6/1993 | DeHarde et al. | 604/198 |
| 5,232,454 | 8/1993 | Hollister | 604/192 |
| 5,312,369 | 5/1994 | Arcusin et al. | 604/192 |
| 5,348,544 | 9/1994 | Sweeney et al. | 604/192 |
| 5,405,332 | 4/1995 | Opalek | 604/263 X |
| 5,445,619 | 8/1995 | Burns | 604/192 |
| 5,466,223 | 11/1995 | Bressler et al. | 604/110 |

*Primary Examiner*—John D. Yasko
*Attorney, Agent, or Firm*—John L. Voellmicke

[57] ABSTRACT

A shield assembly and syringe assembly comprises a syringe assembly including a syringe barrel having a needle cannula projecting distally from its distal end and a shield assembly including a guide and a shield. The guide is secured to a portion of the syringe assembly in proximity to the needle cannula. The shield includes a support wall and a pair of spaced apart side walls projecting from the support wall. At least a portion of the side walls are spaced from one another sufficiently for receiving the needle cannula therebetween. The shield is slidably engaged with the guide and is movable along a path having a generally acute angle with and toward the needle cannula from a proximal position where the needle cannula is exposed to a distal position where the needle cannula is shielded between the side walls of the shield.

17 Claims, 9 Drawing Sheets

FIG-11

MANUALLY DRIVEN NEEDLE SHIELD ASSEMBLY

BACKGROUND OF THE INVENTION

1. Field of the Invention

The subject invention relates to a shield for preventing accidental contact with a needle cannula.

2. Description of the Prior Art

Accidental sticks with the sharply pointed distal end of a needle cannula are painful and can lead to infection. Accidental sticks or other contact with a used needle cannula also may transmit disease.

Most prior art needles have safety shields to prevent accidental sticks. For example, an elongate rigid cap is mounted over most prior art needles prior to use. The cap may be frictionally mounted to the needle hub or to distal portions of a syringe barrel to which the needle is attached. To use the syringe, the health care worker holds the cap in one hand and the syringe barrel in the opposed hand. The respective hands are then moved in opposite directions to separate the cap from the needle.

The used syringe may be shielded by replacing the cap over the needle cannula. However, this shielding operation requires the health care worker to hold the cap in one hand and the used hypodermic syringe in the other hand. The hands then are urged toward one another to replace the cap. A misalignment or sudden movement of either hand can cause the accidental stick. Additionally, the health care worker often must apply pressure to the puncture site of the patient immediately after withdrawing the needle. Thus, the health care worker may not have two free hands available to complete the shielding operation. In these instances, the health care worker may leave the unprotected needle near the patient with intentions to complete the shielding operation at a more convenient time. However, distractions in the health care facility may result in the needle never being properly shielded. The unshielded needle remains a hazard to unsuspecting health care workers and patients.

The prior art also includes safety shields that do not require the health care worker to place a hand in from of the unshielded needle. For example, the prior art includes hypodermic syringes with a rigid tube telescoped over the syringe barrel. These prior art syringes can be used in the conventional manner. The health care worker then holds the extreme proximal end of the syringe barrel in one hand and the shield in the other hand. The shield is then advanced distally along the syringe barrel and is locked into place after the distal end of the shield passes the sharply pointed distal tip of the needle cannula. These shielded hypodermic syringes are an improvement over needle assemblies that require a cap to be telescoped in a proximal direction over the needle cannula. However, the shielded syringes require two-handed actuation.

The prior art also includes smaller shields intended for single handed actuation. One such structure is shown in U.S. Pat. No. 5,466,223. The shield in U.S. Pat. No. 5,466,223 includes a guide structure mounted to the needle hub and an elongated barrier arm slidably mounted in the guide structure. The distal end of the barrier arm includes a barrier element that is telescoped around the needle cannula. This prior art needle shield is used by merely urging the barrier arm distally a sufficient distance for the barrier element to cover and protectively surround the sharply pointed distal tip of the needle cannula.

The barrier shown in U.S. Pat. No. 5,466,223 is effective in preventing accidental sticks with the sharply pointed distal end of a used needle cannula. This barrier also is effective in enabling single handed actuation of the barrier without placing a hand near the tip of the used needle cannula. However, portions of the used needle cannula proximally of the tip remain exposed and can be contacted. In some instances it is desirable to avoid contact with blood or other bodily fluids that may be disposed at intermediate positions along the length of the needle cannula.

SUMMARY OF THE INVENTION

The subject invention is directed to a shield assembly for protectively shielding a needle. The needle may be part of a needle assembly comprising a needle cannula and a hub. The needle cannula may include a proximal end securely mounted to the hub and an opposed sharply pointed distal end. The hub of the needle assembly may be threadedly engageable with a luer collar surrounding the tip of a prior art syringe barrel. Alternatively, the shield assembly of the subject invention may be employed with a prior art hypodermic syringe having a needle cannula permanently affixed thereto and extending from the distal end of the prior art syringe barrel.

The shield assembly of the subject invention includes a guide and a shield. The guide may be securely disposed at a location proximally of the needle cannula. For example, the guide may be rigidly mounted to a needle hub or may be unitarily formed as part of the needle hub. Alternatively, the guide may be securely mounted to or unitarily formed as part of the distal end of a syringe barrel.

The shield is an elongate structure slidably engaged with the guide. The shield includes opposed proximal and distal ends defining an overall length which preferably exceeds the length of the needle cannula to be shielded. The shield includes an elongate substantially rigid support wall extending continuously from the proximal end to the distal end of the shield. Spaced apart side walls project from the support wall and define a narrow space therebetween. The space is wide enough to receive the needle cannula therein, but preferably narrow enough to prevent a finger from being urged between the side walls and into contact with the needle cannula.

The shield and the guide may be configured to slidably move the shield at an acute angle to the axis of the needle cannula. Thus, the shield may be movable from a proximal position where the shield is offset from the axis of the needle cannula to a distal position where the shield intersects the axis of the needle cannula.

The guide and the shield may be configured for achieving linear movement of the shield. Alternatively, the guide and/or the shield may be configured for achieving a non-linear movement. This latter embodiment may permit the shield to remain closer to the syringe barrel when the shield is in its proximal position.

The side walls of the shield may include a pair of flanges slidably engaged with channels formed on the guide. Alternatively, the side walls of the shield may include grooves or slots that are slidably engaged with corresponding structure on the guide.

The shield and the guide may include releasable engagement means for releasably retaining the shield in its proximal position to permit unimpeded use of the needle cannula and the associated syringe.

The shield and the guide may further include cooperating locking structures for locking the shield in a position that prevents inadvertent contact with the needle cannula. For example, the shield may include detents at the proximal end of the shield. The detents may be configured to engage corresponding structure on the guide when the shield has been advanced distally a sufficient distance to substantially enclose the needle. The locking structures may be configured to provide audible and/or tactile indication that the shield has been sufficiently advanced for securely and permanently shielding the needle cannula.

One embodiment of the present invention includes a shield assembly and a syringe assembly comprising a hypodermic syringe assembly which includes a syringe barrel having opposed proximal and distal ends. A needle cannula projects distally from the distal end of the syringe barrel. A shield assembly includes a guide secured to a portion of the syringe assembly in proximity to the needle cannula. A shield is operatively connected to the guide. The shield includes a support wall and a pair of spaced apart side walls projecting from the support walls. At least a portion of the side walls are spaced from one another sufficiently for receiving the needle cannula therebetween. The shield is slidably engaged with the guide and is movable along a path having a generally acute angle with and generally toward the needle cannula from a proximal position where the needle cannula is exposed to a distal position where the needle cannula is shielded between the side walls of the shield.

DETAILED DESCRIPTION OF THE PREFERRED EMBODIMENTS

While this invention is satisfied by embodiments in many different forms, there are shown in the drawings and will be herein described in detail preferred embodiments of the invention with the understanding that the present disclosure is to be considered exemplary of the principals of the invention and is not intended to limit the scope of the invention to the embodiments illustrated. The scope of the invention will be measured by the appended claims and their equivalents.

Figure 1:
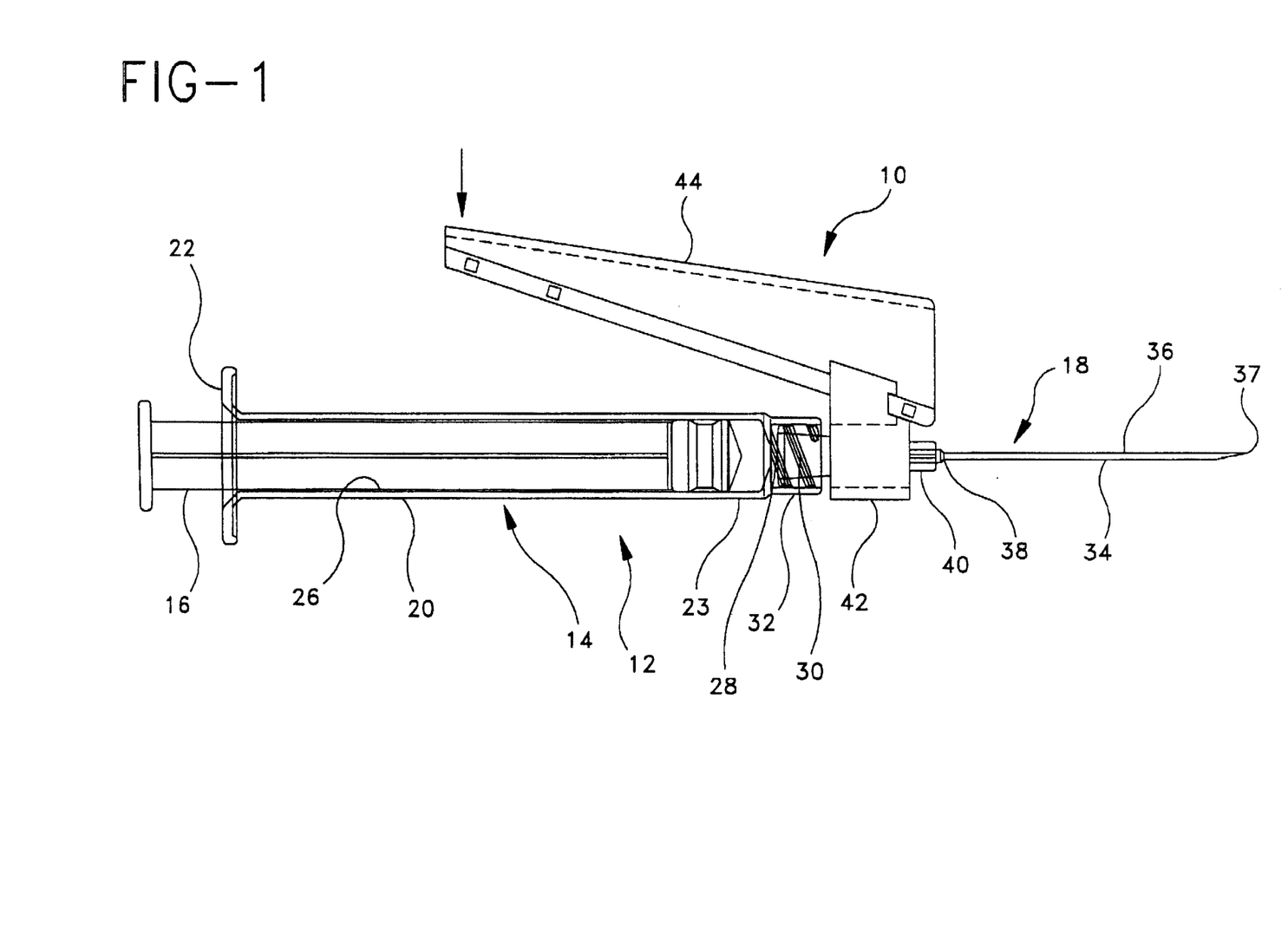
FIG. 1 is a side elevational view of a hypodermic syringe having a shield assembly in accordance with the subject invention securely mounted thereto and disposed in a non-shielding disposition.

A shield assembly in accordance with the subject invention is identified by the numeral 10 in FIG. 1. Shield assembly 10 is used with a prior art hypodermic syringe assembly 12 which comprises a syringe barrel 14, a plunger 16 and a needle assembly 18. Syringe barrel 14 has an elongate tubular side wall 20 with an open proximal end 22, a distal end 23 defined by an inwardly extending shoulder 24 and a fluid receiving chamber between the ends. A tip 28 projects distally from shoulder 24 and includes a passage 30 extending axially therethrough. Passage 30 through tip 28 commnunicates with chamber 26 of the syringe barrel, and enables a flow of fluid into or out of chamber 26. Syringe barrel 14 further includes a luer collar 32 projecting distally from shoulder 24 and surrounding tip 28. Luer collar 32 includes an internal thread.

Plunger 16 is slidably disposed in fluid tight engagement within chamber 26 of syringe barrel 14. Movement of plunger 16 in a proximal direction from the position shown in FIG. 1 urges fluid proximally through passage 30 and into chamber 26. Distal movement of plunger 16 expels fluid from chamber 26.

Needle assembly 18 comprises a needle cannula 34 having a sharply pointed distal end 36 including a sharp tip 37, a proximal end 38 and a lumen extending continuously therebetween. Needle assembly 18 further includes a hub 40 securely mounted to proximal end 38 of needle cannula 34. Hub 40 includes projections that are threadedly engaged with luer collar 32. Thus, hub 40 permits the lumen of needle cannula 34 to be placed in communication with passage 30 through tip 28 of syringe barrel 14.

Figure 2:
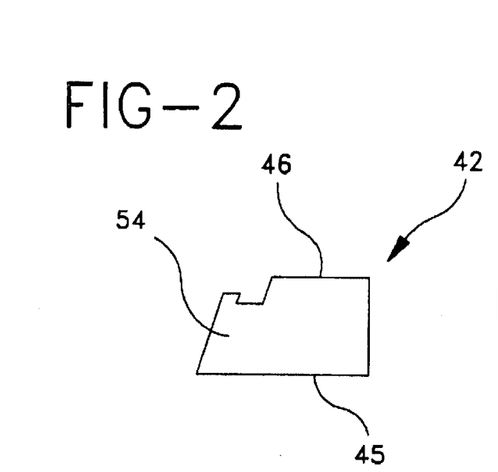
FIG. 2 is a side elevational view of the guide of the shield assembly.
Figure 3:
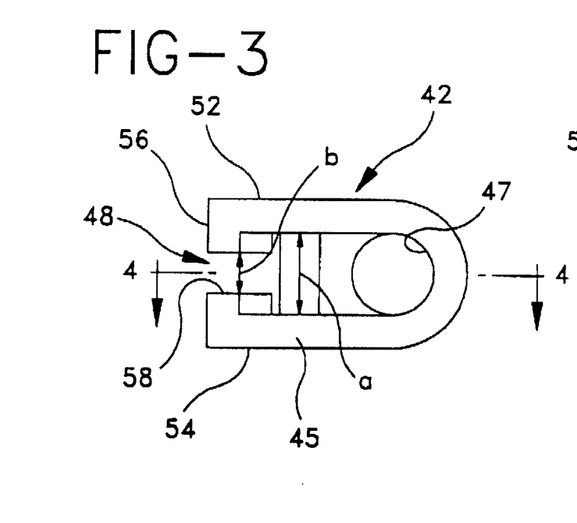
FIG. 3 is a bottom plan view of the guide shown in FIG. 2.
Figure 4:
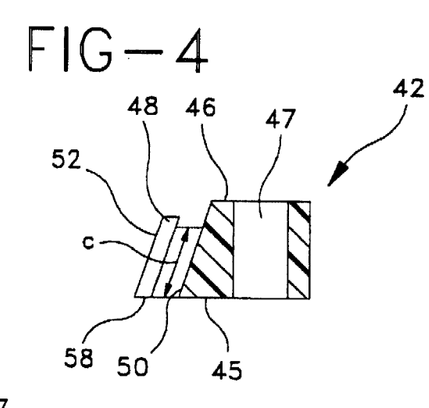
FIG. 4 is a cross-sectional view taken along line 4—4 in FIG. 3.

Shield assembly 10 includes a guide 42 and a shield 44 slidably engaged with guide 42. Guide 42, as shown in FIGS. 2–4 is preferably molded from a plastic material and includes opposed proximal and distal ends 45 and 46. A hub mounting aperture 47 extends between ends 45 and 46 and is dimensioned and configured to be permanently mounted to portions of hub 40 projecting distally beyond luer collar 32. Thus, guide 42 will not impede threaded engagement of hub 40 with luer collar 32.

A shield channel 48 is formed on portions of guide 42 spaced from hub mounting aperture 47. Channel 48 is defined by a bottom surface 50 and a pair of side walls 52 and 54. Portions of side walls 52 and 54 remote from bottom surface 50 include inwardly projecting flanges 56 and 58. Thus, channel 48 defines a major width "a" adjacent bottom surface 50 and a minor width "b" between flanges 56 and 58. As shown most clearly in FIG. 4, channel 48 is aligned at an acute angle to hub mounting aperture 47 and defines a length "c". As will be explained further below, the acute angle of channel 48 enables shield 44 to be slid toward needle cannula 34.

Figure 5:
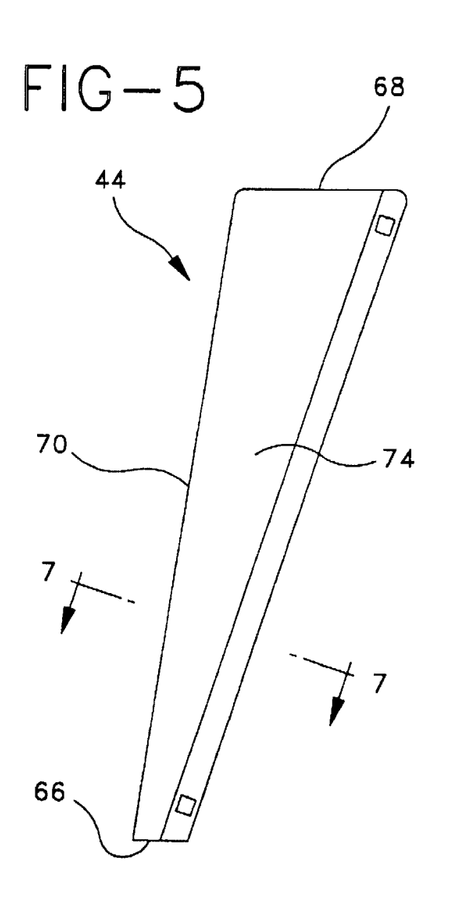
FIG. 5 is a side elevational view of the shield shown in FIG. 1.
Figure 6:
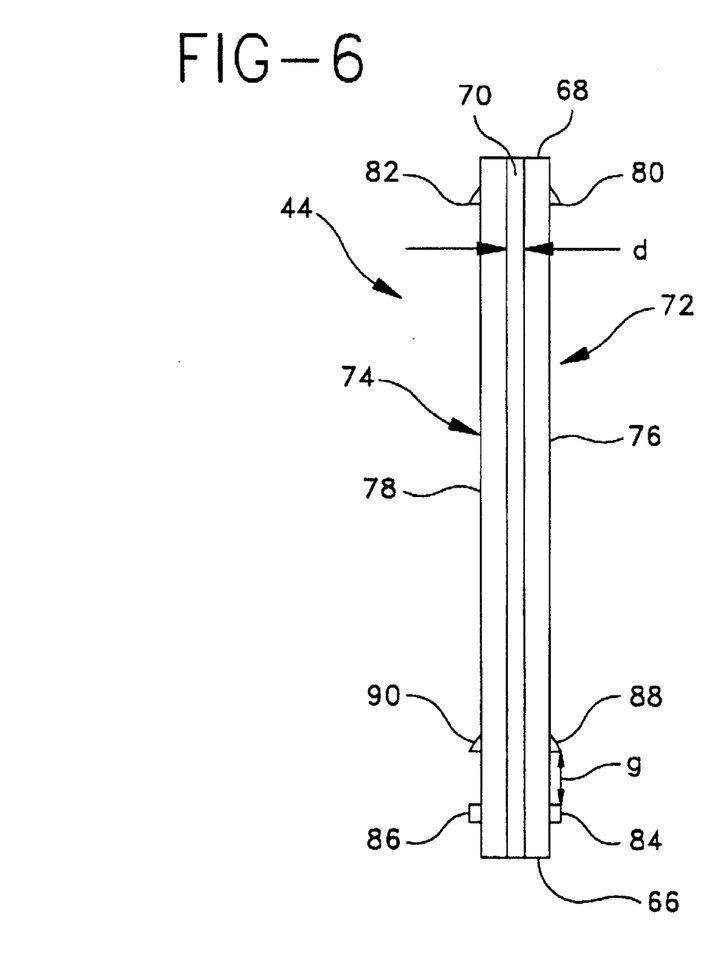
FIG. 6 is a front elevational view of the shield shown in FIG. 1.
Figure 7:
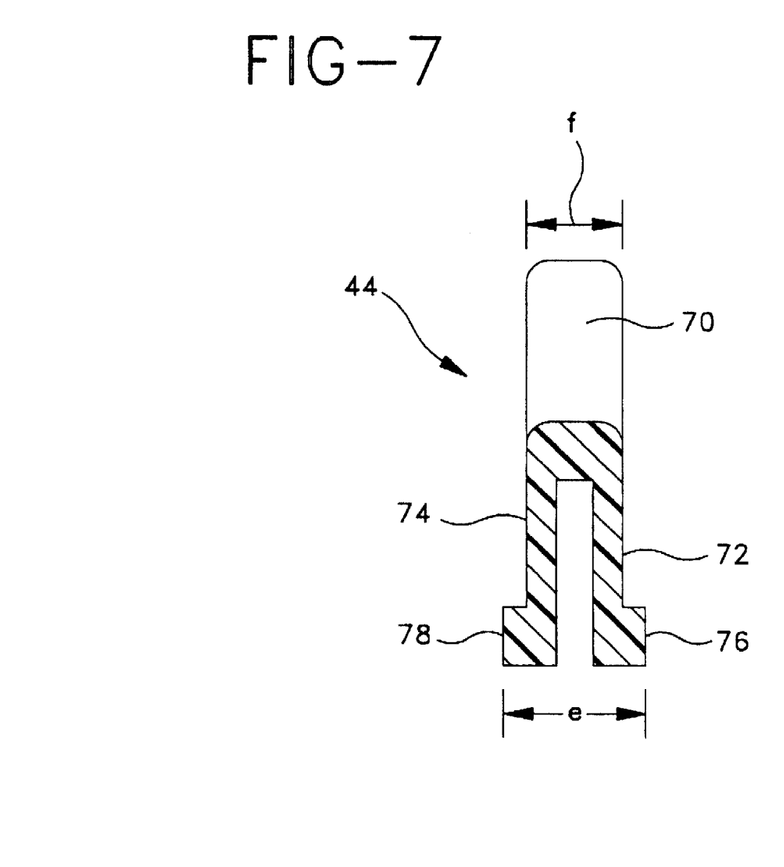
FIG. 7 is a cross-sectional view taken along line 7—7 in FIG. 5.

Shield 44, as shown most clearly in FIGS. 5–7, is preferably unitarily molded from a rigid plastic and includes a proximal end 66 and an opposed distal end 68. A support wall 70 extends continuously from proximal end 66 to distal end 68, and side walls 72 and 74 extend rigidly from support wall 70 in spaced parallel relationship to one another. Side walls 72 and 74 are spaced from one another by distance "d", as shown in FIG. 6. Dimension "d" is sufficiently great to permit needle cannula 18 to be received between side walls 72 and 74, but is sufficiently narrow to prevent insertion of a finger. Side walls 72 and 74 of this embodiment are desirably, but not necessarily, of generally trapezoidal shape and define a minor width adjacent proximal end 66 and a major width adjacent distal end 68.

Side walls 72 and 74 are formed with outwardly extending flanges 76 and 78 on portions remote from support wall 70. Flanges 76 and 78 define a major outside width "e", as shown in FIG. 7, which is slightly less than the major width "a" of channel 48, but greater than the minor width "b" of channel 48. Portions of side wall 72 and 74 spaced from flanges 76 and 78 define a minor outside width "f", as shown in FIG. 7, which is slightly less than the minor width "b" of channel 48. Thus, flanges 76 and 78 of shield 44 can be slidably received in the major width portions of channel 48, while portions of side walls 72 and 74 adjacent flanges 76 and 78 can be slidably received between flanges 56 and 58 of guide 42.

Flanges 76 and 78 are formed with ramped retention projections 80 and 82 adjacent distal end 68. Ramped retention projections 80 and 82 include distally facing surfaces inclined to flanges 76 and 78 and proximally facing locking surfaces orthogonal to flanges 76 and 78.

Flanges 76 and 78 further include stop projections 84 and 86 substantially adjacent proximal end 66. Stop projections 82 include distally facing surfaces that extend substantially orthogonal to flanges 76 and 78.

Ramped locking projections 88 and 90 extend outwardly from flanges 76 and 78 at a location thereon spaced a distance "g" distally from stop projections 84 and 86. Locking projections 88 and 90 include distally facing surfaces inclined to flanges 76 and 78 at an acute angle and proximally facing surfaces orthogonal to flanges 76 and 78. Distance "g" is slightly greater than length "c" of channel 48 in guide 42.

Shield assembly 10 is assembled by sliding needle assembly 18 into hub aperture 47 of guide 42. Sufficient distal movement of needle assembly 18 will securely lock or capture hub 40 in guide 42. Shield 44 is then urged in a distal direction into channel 48 of guide 42. More particularly, distal end portions of flanges 76 and 78 are urged into portions of channel 48 between bottom surface 50 and flanges 56 and 58 thereof. The inclined surfaces of retention projections 80 and 82 will deflect side walls 52 and 54 of guide 42 away from one another sufficiently for retention projections 80 and 82 to pass through channel 48. Side walls 52 and 54 will resiliently return toward an undeflected condition when retention projections 80 and 82 pass distally beyond guide 42. Projections 80 and 82 cooperate with the guide to function as a means for preventing the shield from moving proximally from the proximal position out of engagement with the guide. Other projections not shown could be placed inwardly from projections 80 and 82 at a distance longer than said guide to provide means for retaining the guide in its retracted proximal needle exposing position. Sufficient force would have to be applied to the guide to move the guide distally and overcome the resistance of the additional projections and the guide channel. Flanges 56 and 58 of guide 42 then will preferably frictionally engage side walls 72 and 74 of shield 44. These frictional forces will prevent shield 44 from inadvertently sliding distally relative to guide 42. Although a slight frictional engagement between the shield and the guide is preferred it is not necessary to carry out the present invention. The frictional forces prevent the guide from moving inadvertently. This same result can be accomplished by having projections on the guide or the shield and recesses or other projections on the other element so that motion of the shield is slightly impeded. However, for the locking functions a more aggressive snap-fit arrangement as taught is preferred. All of these structures come within the purview of the present invention. Simultaneously, the proximally facing surfaces of retention projections 80 and 82 will help prevent shield 44 from being removed proximally from channel 48 in guide 42. A protective cap (not shown) may be mounted over needle cannula 34 and in frictional engagement with guide 42. The protective cap will prevent accidental sticks prior to use of syringe assembly 12.

The protective cap may be removed shortly prior to use of syringe assembly 12. Syringe assembly 12 may then be used in the conventional manner by initially drawing a selected medication into fluid receiving chamber 26 and subsequently injecting the medication into a patient. As noted above, portions of needle cannula 34 near distal tip 36 may have been exposed to infectious bodily fluids and are capable of transmitting diseases.

Figure 8:
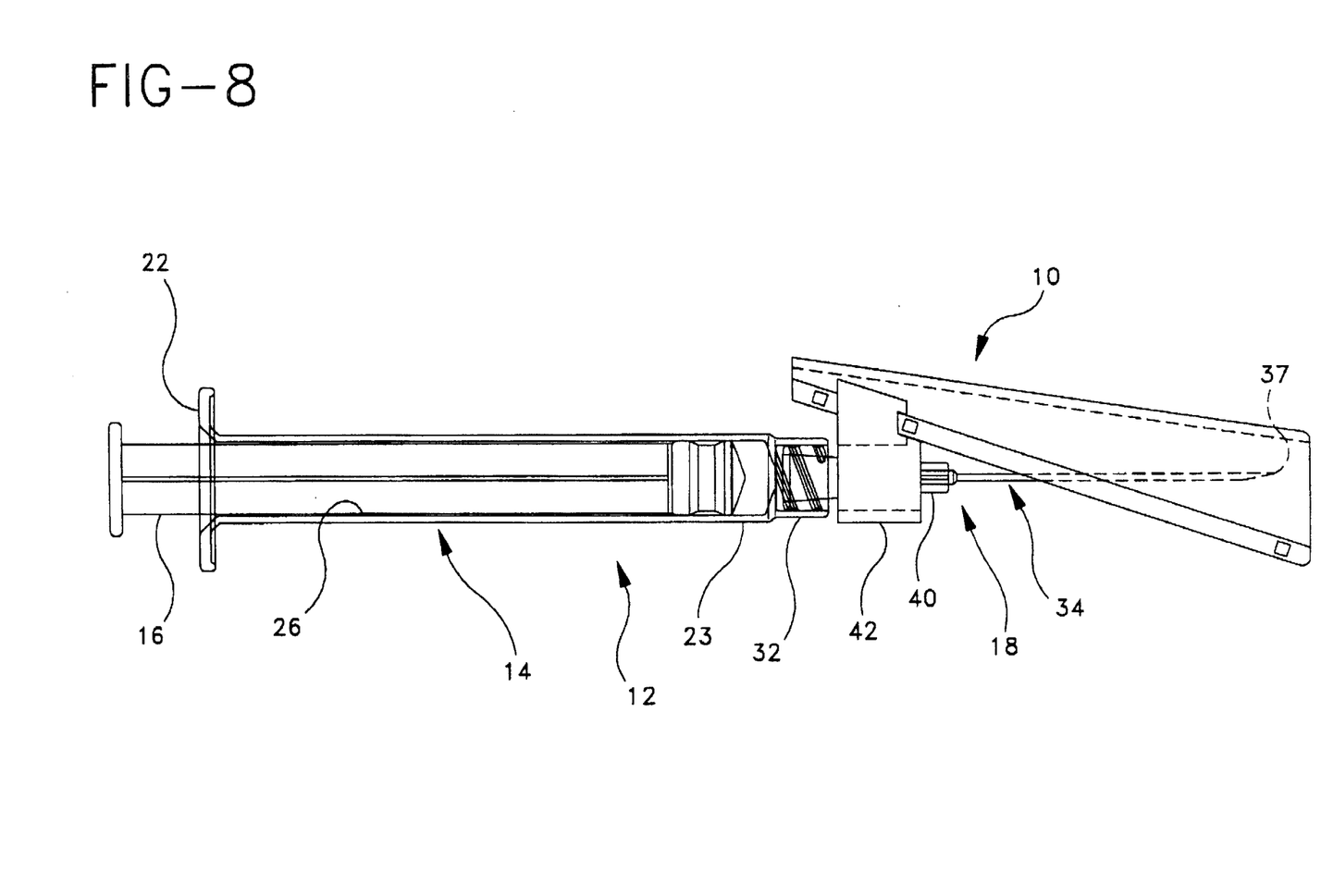
FIG. 8 is a side elevational view similar to FIG. 1 but showing the shield in an alternate position relative to the guide and the hypodermic syringe.

After use of syringe assembly 12, digital forces can be exerted on proximal end 66 of shield 44 by the thumb or forefinger of the hand holding syringe barrel 14. These distally directed digital forces on shield 44 will overcome frictional forces between shield 44 and guide 42 and will urge shield 44 distally relative to guide 42. Sufficient distal movement of shield 44 relative to guide 42 will cause locking projections 84 and 86 of shield 44 to contact side walls 52 and 54 of guide 42. The inclined surfaces of projections 84 and 86 will generate sufficient deflection of side walls 52 and 54 to enable further movement of shield 44. After sufficient distal movement, locking projections 84 and 86 will pass distally beyond guide 42, thereby permitting side walls 52 and 54 to resiliently return to an undeflected condition. Although the preferred embodiment relies on deflection of the side walls it is within the purview of the present invention to design the joining parts to that either the shield or the guide is the deflecting member or that the parts are designed so that both elements deflect slightly to achieve the desired result. The structure described hereinabove is merely preferred and not intended to limit the invention. Further distal movement of shield 44 is positively prevented by contact between the surfaces of stops 88 and 90 on flanges 76 and 78 with proximal end 45 of guide 42. movement of shield 44 that could re-expose needle cannula 34 is prevented by the proximal surfaces of locking projections 84 and 86. Thus, shield 44 is positively locked in the position shown in FIG. 8 with needle cannula 34 safely positioned between side walls 72 and 74 of shield 44. The used syringe assembly may then be discarded in a conventional sharps receptacle.

Figure 9:
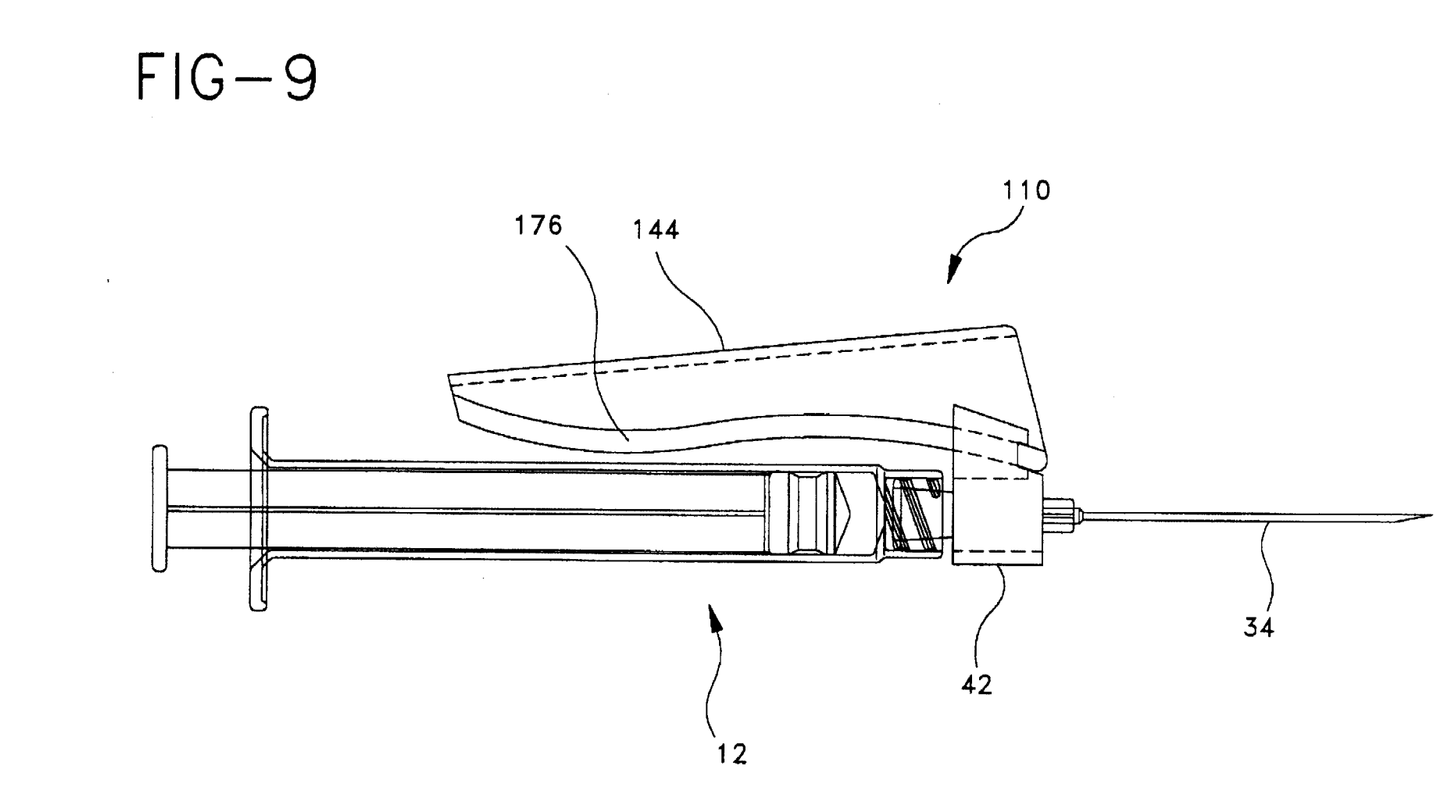
FIG. 9 is a side elevational view similar to FIG. 1, but showing a second embodiment of the shield assembly.
Figure 10:
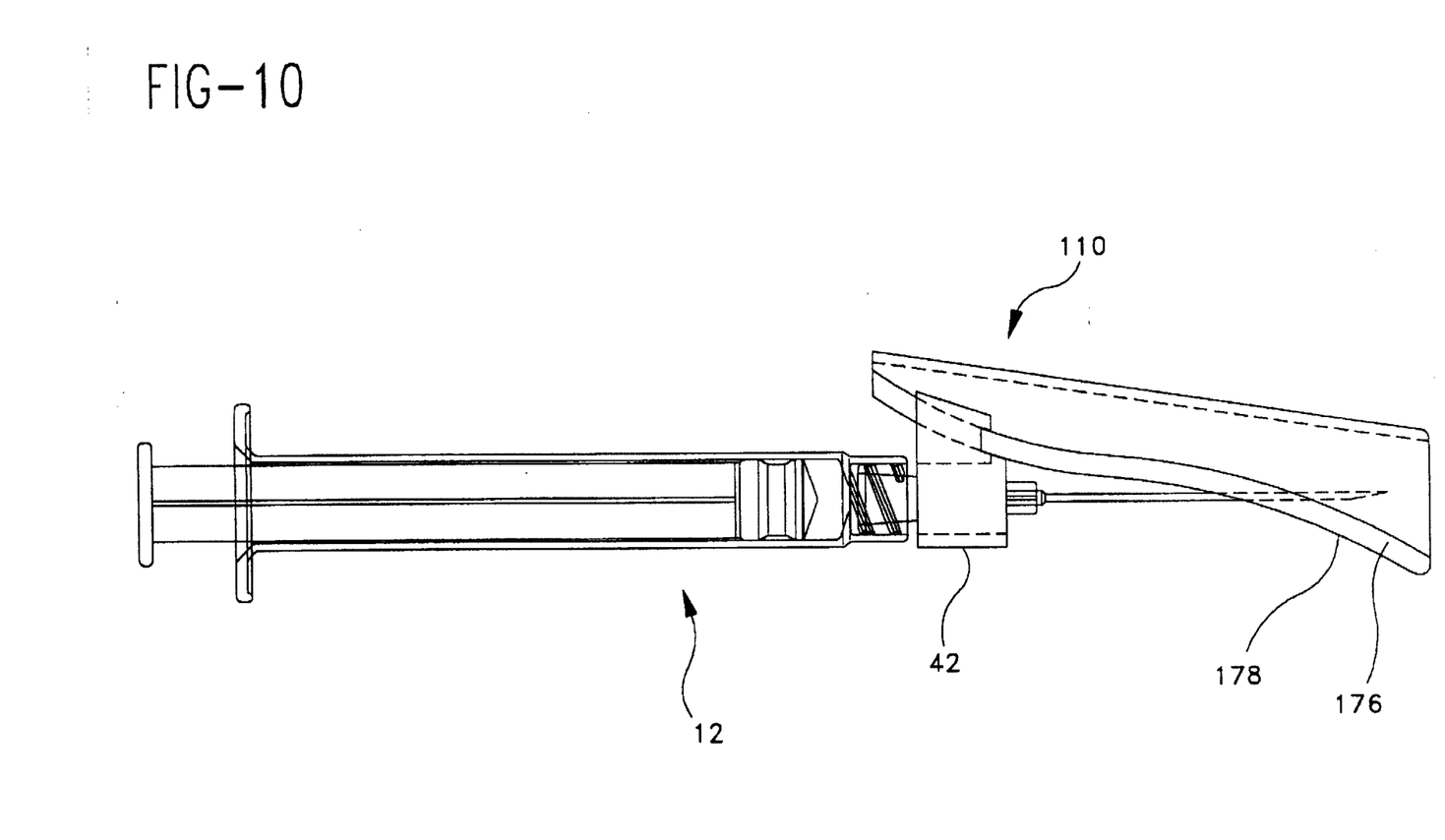
FIG. 10 is a side elevational view similar to FIG. 8, but showing the second embodiment of the shield assembly.

FIGS. 9 and 10 show a second embodiment of a shield assembly which is identified by the numeral 110. Shield assembly 110 is mounted to the above described syringe assembly 12, and includes a guide 42 substantially identical to the guide described and illustrated above. However, shield assembly 110 includes a shield 144 with non-linear flanges 176 and 178 formed thereon. Non-linear or curvilinear flanges 176 and 178 enable shield 144 to travel in a non-linear or curvilinear path between the proximal position shown in FIG. 9 and the distal position shown in FIG. 10. The curvilinear shape of flanges 176 and 178 enables shield 144 to remain closer to syringe barrel 14, and hence defines a smaller cross-sectional dimension in the ready-to-use proximal position of FIG. 9 as compared to the comparable position of the shield assembly 10 shown in FIG. 1. However, as shown in FIG. 10, shield 144 achieves approximately the same shielding protection of needle cannula 34 as the above described shield 44. Allowing the shield to move in a non-linear or curvilinear path along a generally acute angle toward the needle cannula is an important feature of the present invention. The position of the shield at the proximal and distal positions can be optimized. At the distal position, the shield can move sharply toward the needle cannula so that the cannula is deep within the shield and well protected when the shield is in the distal position. Also, through the curvilinear motion, the shield can take its proximal position very close to the barrel of the syringe and be less obtrusive during the normal operation of the syringe.

With the curvilinear flanges on the shield the direction of the groove does not necessarily have to be angled with respect to the needle and can be parallel with the needle. The path of the shield with respect to the needle follows a generally acute path toward the needle as the shield moves toward its needle protecting position.

Figure 11:
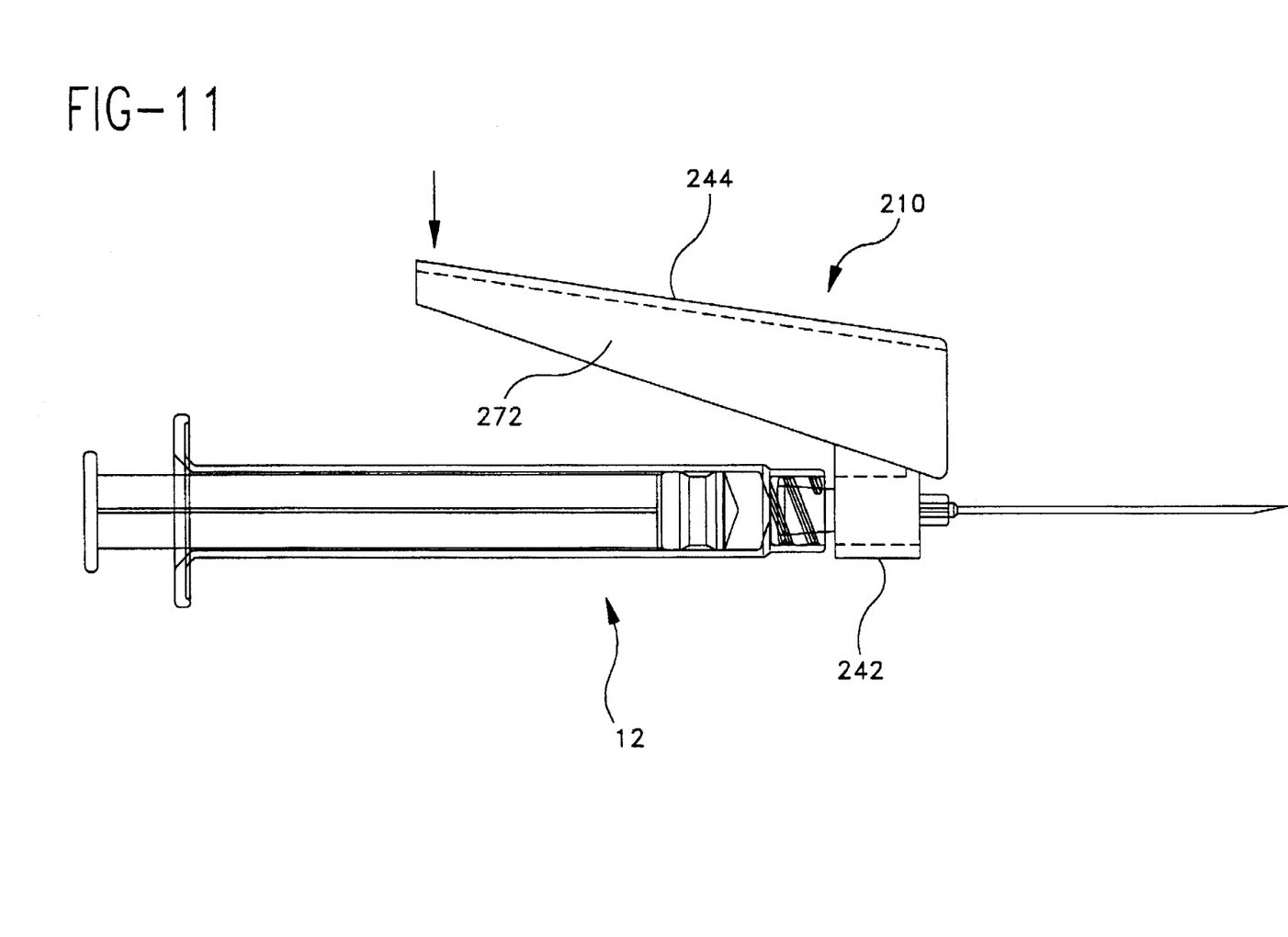
FIG. 11 is a side elevational view similar to FIG. 1 but showing a third embodiment of the shield assembly.
Figures 12, 14:
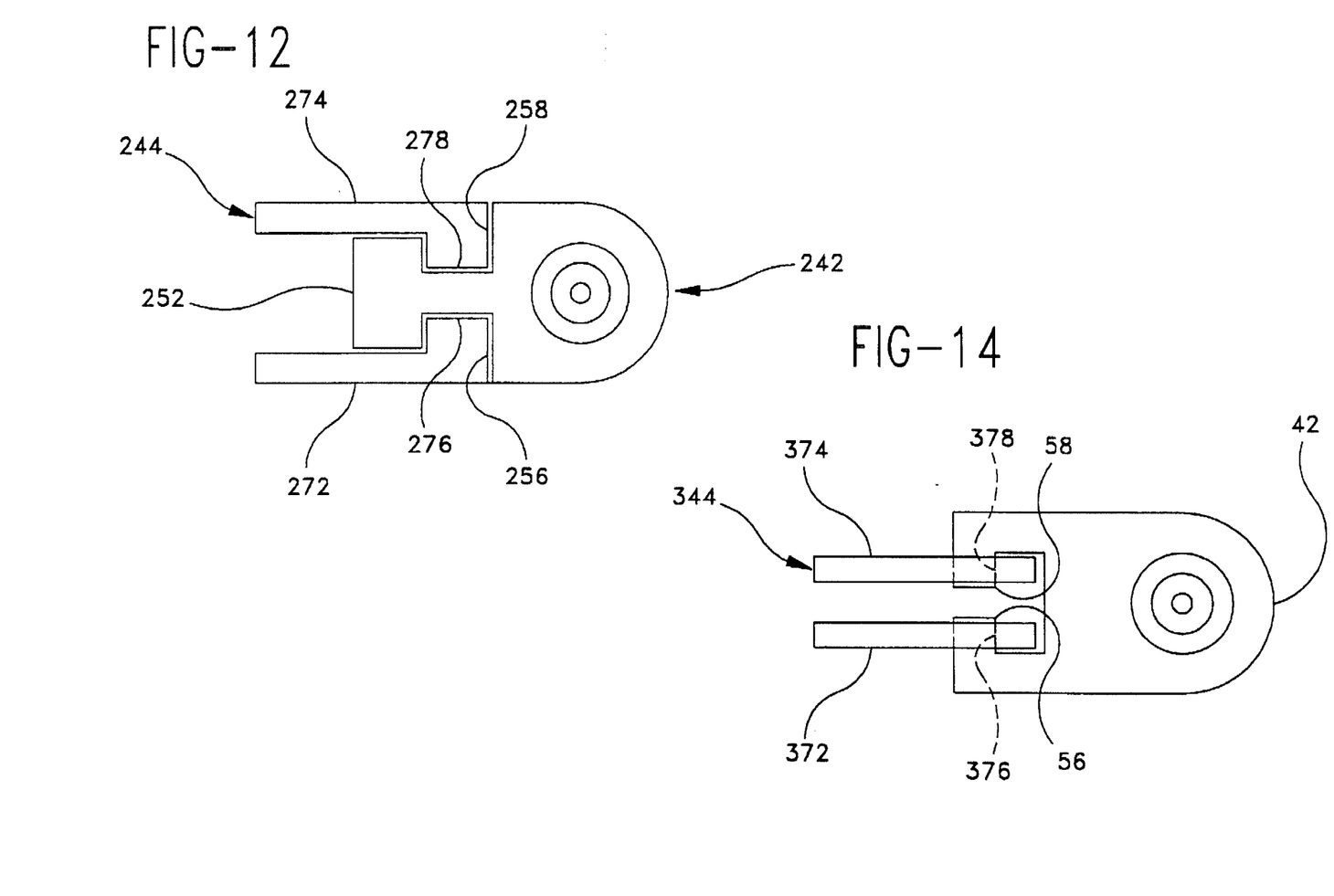
FIG. 12 is a top plan view of the assembly shown in FIG. 11.
FIG. 14 is a top plan view of the assembly shown in FIG. 13.

A third embodiment of the shield assembly is shown in FIGS. 11 and 12, and is identified by the numeral 210. Shield assembly 210 includes a guide 242 with a single side wall 252 and a pair of channels 256 and 258 formed therein. Shield assembly 210 further includes a shield 244 with side walls 272 and 274 having inwardly projecting flanges 276 and 278 dimensioned for receipt in channel 256 and 258 of guide 242. In all functional respects, shield assembly 210 operates in similar manner as the shield assembly 210 described above and illustrated in FIGS. 1–7.

Figure 13:
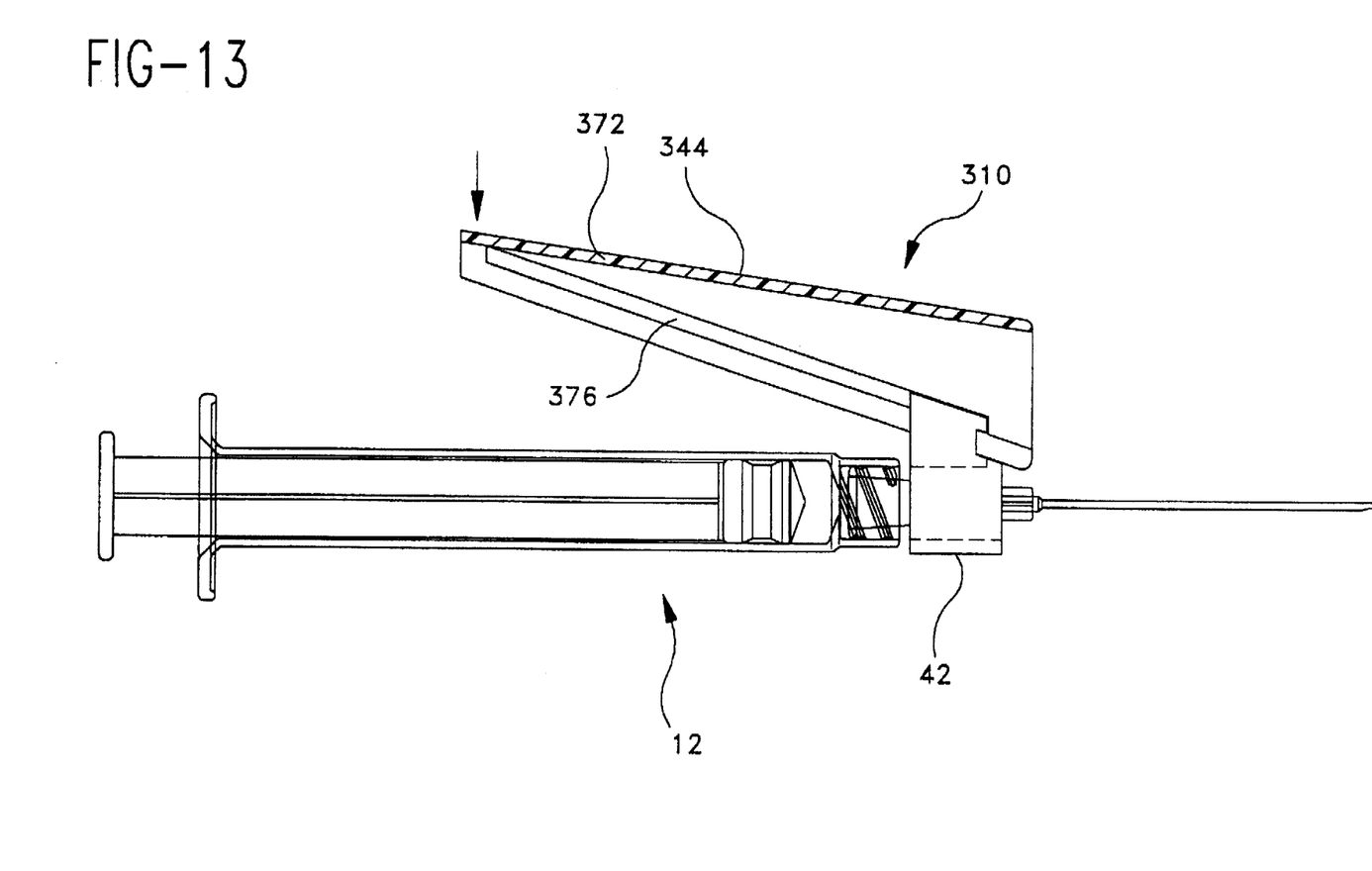
FIG. 13 is a side elevational view similar to FIG. 1 but showing a fourth embodiment of the shield assembly.

A fourth embodiment of the shield assembly is shown in FIGS. 13 and 14 and is identified generally by the numeral 310. Shield assembly 310 includes a guide 42 substantially as described and illustrated above. Shield assembly 310 further includes a shield 344 with side walls 372 and 374. Side walls 372 and 374 are not formed with flanges as in the preceding embodiment. Rather, side walls 372 and 374 are formed with elongate slots 376 and 378 extending entirely therethrough. Slots 376 and 378 are dimensioned to receive flanges 56 and 58 of guide 42. In all other respects, shield assembly 310 functions similarly to shield 10 described above and illustrated in FIGS. 1–7.

What is claimed is:

1. A shield assembly and syringe assembly comprising:
   a syringe assembly including a syringe barrel having opposed proximal and distal ends, a needle cannula projecting distally from said distal end of said syringe barrel; and
   a shield assembly including a guide secured to a portion of said syringe assembly in proximity to said needle cannula, and a shield having a support wall and a pair of spaced apart side walls projecting from said support wall, said side walls being spaced from one another sufficiently for receiving said needle cannula therebetween, said shield being slidably engaged with said guide and being movable along a path having a generally acute angle with and toward said needle cannula, from a proximal position where said needle cannula is exposed to a distal position where said needle cannula is shielded between said side walls of said shield.

2. The assembly of claim 1, further comprising locking means for locking said shield in said distal position.

3. The assembly of claim 1, further including means for preventing said shield from moving proximally from said proximal position out of engagement with said guide.

4. The assembly of claim 1, wherein said guide includes a pair of spaced apart side walls, said side walls of said shield being slidably engaged between said side walls of said guide.

5. The assembly of claim 4, wherein said side walls of said guide define a channel, said channel having a bottom surface extending between said side walls, said side walls of said guide further including a pair of flanges projecting toward one another at locations on said side walls spaced from said bottom surface of said channel, said side walls of said shield being slidably engaged with said flanges of said side walls on said guide.

6. The assembly of claim 5, wherein said side walls of said shield include a pair of outwardly extending flanges slidably engaged in portions of said channel between said bottom surface and said flanges of said guide.

7. The assembly of claim 5, wherein said side walls of said shield each include an elongate slot, said flanges of said side walls of said guide being slidably engaged in said slots of said side walls of said shield.

8. The assembly of claim 1, wherein said shield includes opposed proximal and distal ends, said side walls being substantially trapezoidal and having a major width substantially adjacent said distal end of said shield and a minor width substantially adjacent said proximal end of said shield.

9. The assembly of claim 1, wherein said guide includes a pair of side channels facing oppositely on said guide, said shield including a pair of flanges projecting toward one another on said respective side walls, said flanges of said side walls being slidably engaged within said channels of said guide.

10. A assembly of claim 9, wherein said channels of said guide are aligned to said needle cannula at an acute angle for selectively guiding said shield distally and toward said needle cannula.

11. The assembly of claim 1, wherein said guide and said shield are configured for non-linear sliding movement of said shield relative to said guide.

12. The assembly of claim 1, wherein said hypodermic syringe assembly includes a needle hub securely connected to said needle cannula and releasably engageable with said syringe barrel, said guide being connected to said hub.

13. The assembly of claim 1 further including means for controlling said path of said shield between said proximal position and said distal position so that said path is curvilinear.

14. A shieldable hypodermic syringe assembly comprising:
    a syringe barrel having opposed proximal and distal ends, a luer collar projecting distally from said distal end and having an internal thread;
    a needle assembly having a hub threadedly engaged with said luer collar such that a portion of said hub projects distally beyond said luer collar, said needle assembly further having a needle cannula with a proximal end securely engaged in said needle hub and a sharply pointed distal end;
    a guide connected to said portion of said hub projecting distally beyond said luer collar, said guide including at least one guide wall angularly aligned toward said needle cannula; and
    a shield having a support wall and a pair of side walls projecting from said support wall and being spaced from one another by a distance sufficient for receiving said needle cannula therebetween, said side walls being slidably engaged with said guide wall of said guide and being movable along a path having a generally acute angle with and toward said needle cannula from a proximal position where said shield is spaced proximally from said distal end of said needle cannula to a distal position where said needle cannula is protectively shielded between said support wall and said side walls of said shield.

15. The hypodermic syringe assembly of claim 14, wherein said shield and said guide include locking means for securely locking said shield in said distal position.

16. The hypodermic syringe assembly of claim 15, wherein said guide and said shield include retention means for releasably engaging said shield in said proximal position.

17. The hypodermic syringe assembly of claim 14, wherein said shield and said guide are configured for maintaining said shield transversely offset from said needle cannula when said shield is in said proximal position.

* * * * *